(12) United States Patent
Yamamoto et al.

(10) Patent No.: US 10,264,966 B2
(45) Date of Patent: Apr. 23, 2019

(54) OPHTHALMIC DEVICE

(71) Applicant: Tomey Corporation, Nagoya-shi (JP)

(72) Inventors: Shigeyoshi Yamamoto, Nagoya (JP); Guangchun Bian, Nagoya (JP)

(73) Assignee: Tomey Corporation, Aichi-Ken (JP)

( * ) Notice: Subject to any disclaimer, the term of this patent is extended or adjusted under 35 U.S.C. 154(b) by 90 days.

(21) Appl. No.: 15/257,093

(22) Filed: Sep. 6, 2016

(65) Prior Publication Data

US 2017/0065174 A1 Mar. 9, 2017

(30) Foreign Application Priority Data

Sep. 7, 2015 (JP) ................................ 2015-175264

(51) Int. Cl.
*A61B 3/00* (2006.01)
*A61B 3/15* (2006.01)
*A61B 3/16* (2006.01)
*A61B 3/18* (2006.01)
*A61B 3/103* (2006.01)

(52) U.S. Cl.
CPC .............. *A61B 3/18* (2013.01); *A61B 3/0091* (2013.01); *A61B 3/103* (2013.01); *A61B 3/152* (2013.01); *A61B 3/16* (2013.01); *A61B 3/165* (2013.01)

(58) Field of Classification Search
CPC ....... A61B 3/0083; A61B 3/0091; A61B 3/10; A61B 3/102–3/103; A61B 3/107; A61B 3/1015; A61B 3/1025; A61B 3/117; A61B 3/1225; A61B 3/14; A61B 3/145; A61B 3/15; A61B 3/152; A61B 3/18; A61B 3/16; A61B 3/165

USPC ........ 351/200, 205, 206, 208–210, 212, 245
See application file for complete search history.

(56) References Cited

U.S. PATENT DOCUMENTS

| 5,523,808 | A | 6/1996 | Kohayakawa |
| 2009/0128778 | A1 | 5/2009 | Honda et al. |
| 2013/0271727 | A1 | 10/2013 | Park et al. |
| 2013/0293837 | A1 | 11/2013 | Akiba |

FOREIGN PATENT DOCUMENTS

| JP | H6-047003 A | 2/1994 |
| JP | 2006-055200 A | 3/2006 |
| JP | 2007-282670 A | 11/2007 |
| JP | 2007-289662 A | 11/2007 |
| JP | 2007-289663 A | 11/2007 |
| JP | 2013-220196 A | 10/2013 |
| JP | 2013-230303 A | 11/2013 |

*Primary Examiner* — Thomas K Pham
*Assistant Examiner* — Ibrahima Diedhiou
(74) *Attorney, Agent, or Firm* — Shumaker, Loop & Kendrick, LLP

(57) ABSTRACT

An ophthalmic device is configured to examine at least two eye characteristics including intraocular pressure, and the ophthalmic device includes: an examination optical system configured to obtain information of a subject's eye when the at least two eye characteristics of the subject's eye are examined; and an examination window configured to switch examinations of the at least two eye characteristics. The examination optical system is arranged outside of the examination window. The examination window is capable of rotating independently of the examination optical system. The examinations of the at least two eye characteristics are switched by rotation of the examination window.

8 Claims, 7 Drawing Sheets

OPHTHALMIC DEVICE

CROSS-REFERENCE TO RELATED APPLICATION

This application claims priority in Japanese Patent Application No. 2015-175264 filed on Sep. 7, 2015, the entire contents of which are hereby incorporated by reference into the present application.

TECHNICAL FIELD

The present disclosure relates to an ophthalmic device configured to examine at least two eye characteristics including tonometry (i.e., intraocular pressure examination).

DESCRIPTION OF RELATED ART

As an ophthalmic device that examines a plurality of eye characteristics for an eye to be examined (hereinafter, "a subject's eye"), a device that has a tonometry unit configured to measure intraocular pressure in non-contact and an eye refractive power measurement unit (hereinafter "eye refraction test unit") configured to measure refractive power, and conducts measurements by switching between them is disclosed in for example, Japanese Patent Application Publication No. 2013-230303.

Japanese Patent Application Publication No. 2013-230303 discloses, a configuration that has a first eye examination unit (e.g., tonometry) and a second eye examination unit (e.g., refraction test), and rotates a switching unit that includes an optical element (a mirror in the embodiment) shared by the two examination units to change an orientation of the optical element so as to switch optical paths to the first eye examination unit or the second eye examination unit.

SUMMARY

In the configuration disclosed in Japanese Patent Application publication No. 2013-230303, the optical element disposed in the switching unit that rotates and shared for the two characteristics, for example, a mirror has its orientation changed in accordance with the rotation of the switching unit so that the optical paths are switched, thereby switching between the tonometry (the first eye examination unit) and the refraction test (the second eye examination unit). That is, the switching unit is rotated with a center of the mirror as a rotation axis.

Due to this, in the configuration disclosed in Japanese Patent Application Publication No. 2013-230303 which rotates the switching unit around the center of the mirror, which is the shared optical element, as the rotation axis, there is a fear that a position displacement of the shared mirror might occur, leading to a displacement of a measurement optical axis and deteriorating accuracy of a targeted eye characteristic examination.

In order to solve the above problem, an ophthalmic device disclosed herein is configured to examine at least two eye characteristics including intraocular pressure, the ophthalmic device comprising: an examination optical system configured to obtain examination information of a subjects eye when the at least two eye characteristics of the subject's eye are examined; and an examination window configured to switch examinations of the at least two eye characteristics. The examination optical system is arranged outside of the examination window. The examination window is capable of rotating independently of the examination optical system. The examinations of the at least two eye characteristics are switched by rotation of the examination window.

As will be described in detail below, the examination window in the present disclosure does not have an optical element that is shared by a first eye examination unit and a second eye examination unit and changes the optical paths as in the Japanese Patent Application Publication No. 2013-230303. Therefore, when the examinations of the eye characteristics are switched by rotating the examination window in the present disclosure, optical paths are not changed in the examination window. That is, because the examination window only rotates upon switching the examinations, switching the examinations can be conducted in a simple manner while suppressing the displacement, of the optical axis due to a rotation of the examination window.

In the ophthalmic device disclosed herein, the examination window may comprise an inflow hole into winch air flows from outside of the examination window when the intraocular pressure is examined, and the examination window may be configured to rotate around a center axis of the inflow hole.

By rotating the examination window around the air passage for the intraocular pressure as the rotation axis, the rotation of the examination window does not cause the air passage for the intraocular pressure to move, thereby enabling a stable amount of air to be puffed toward the subject's eye in the tonometry, and deterioration of examination accuracy can be prevented.

In the ophthalmic device herein, the at least two eye characteristics may include a first eye characteristic and a second eye characteristic different from the first eye characteristic, the second eye characteristic being the intraocular pressure. The examination optical system may comprise: a first examination optical system used to examine the first eye characteristic; and a second examination optical system used to examine the second eye characteristic. The examination window may be capable of switching between a first state and a second state different from the first state. The first eye characteristic may be examined by using the examination window and the first examination optical system when the examination window is in the first state. The second eye characteristic may be examined by using the examination window and the second examination optical system when the examination window is in the second state.

In the ophthalmic device herein, the examination optical system may comprise a common observation optical system configured to serve as: a first observation optical system configured to observe the subject's eye when the first eye characteristic is examined; and a second observation optical system configured to observe the subject's eye when the second eye characteristic is examined.

In the ophthalmic device herein, the examination optical system may comprise a common index optical system (fixation optical system) configured to serve as: a first index optical system (fixation optical system) configured to cause the subject's eye to fixate when the first eye characteristic is examined, and a second index optical system (fixation optical system) configured to causes the subject's eye to fixate when the second eye characteristic is examined.

In the ophthalmic device herein, the examination optical system may comprise a common alignment optical system configured to serve as a first alignment optical system configured to conduct alignment when the first eye characteristic is examined, and a second alignment optical system configured to conduct alignment when the second eye characteristic is examined.

An observation optical system, an index optical system, and an alignment optical system are essential elements for examining an eye characteristic. One or more elements of these can be shared for several eye characteristics depending on what eye characteristic to be examined. In such a case, a whole optical system can be made compact by configuring the whole optical system so as to share one or more of these optical systems, as a result of which device miniaturization and cost reduction can be realized.

According to the present disclosure, because the optical axis displacement and fluctuation in the amount of air in the tonometry, that often happen when switching the examinations of eye characteristics, are suppressed with a simple configuration, the switching of the examinations for at least two characteristics including a tonometry can be conducted promptly, resulting in the reduction of examination time and reducing load imposed upon a patient.

DETAILED DESCRIPTION

With reference to the drawings, an ophthalmic device according to an embodiment of the present disclosure will be described below.

Embodiment

Figure 1:
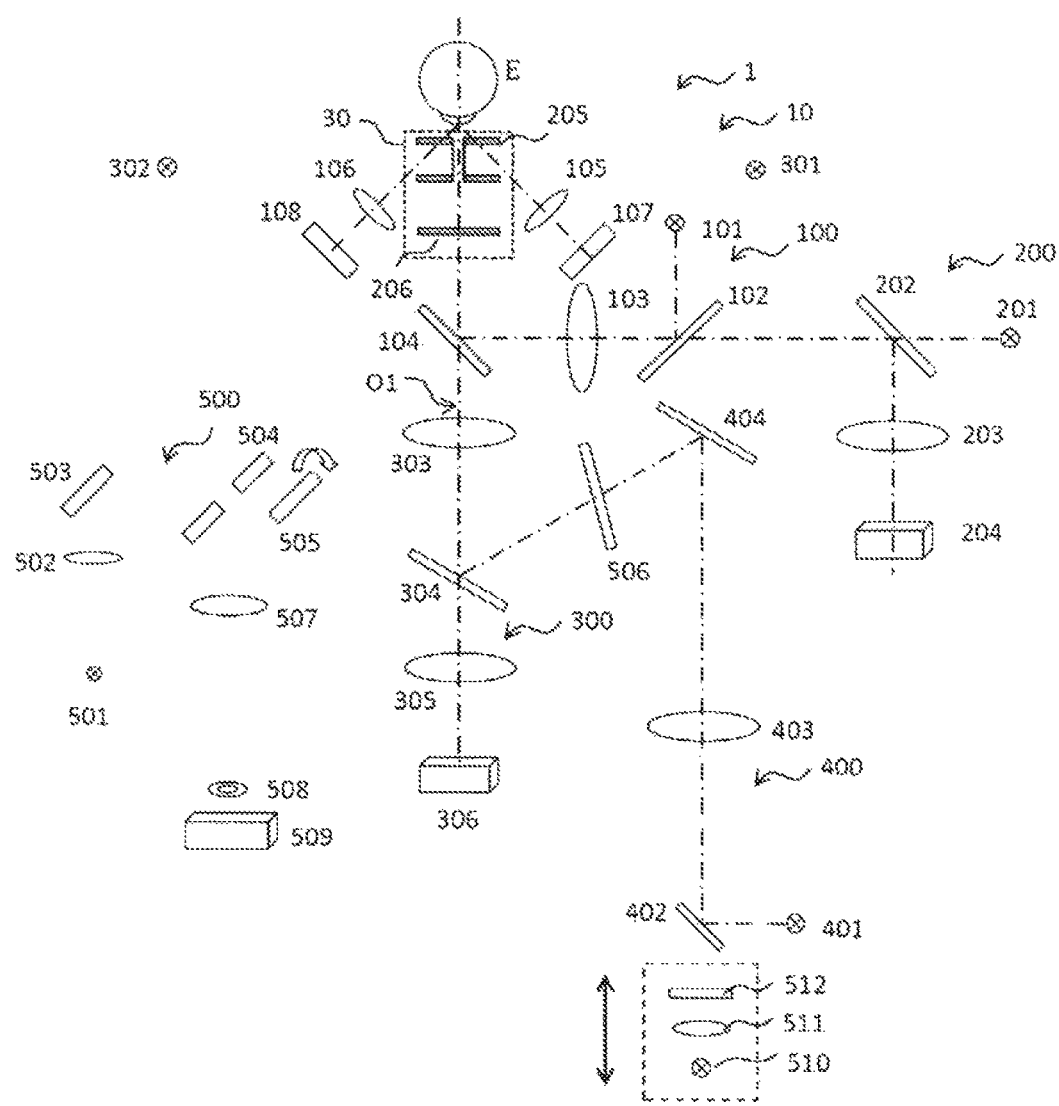
FIG. 1 is a schematic configuration diagram of a tonometry optical system 10 an ophthalmic device according to an embodiment of the present application.
Figure 2:
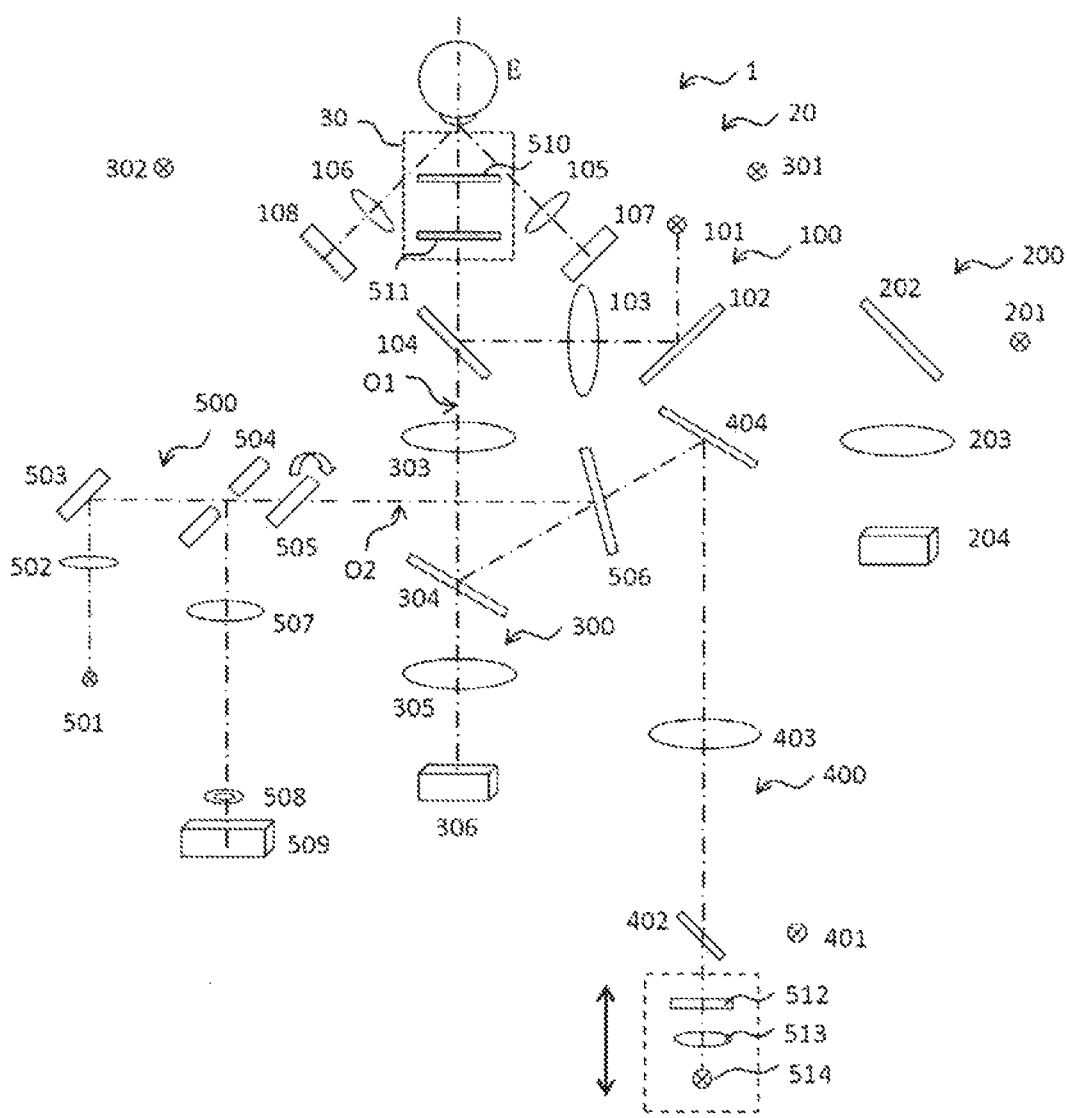
FIG. 2 is a schematic configuration diagram of an eye refraction test optical system 20 of the ophthalmic device according to the embodiment.

FIGS. 1 and 2 are diagrams which illustrate details of optical systems of an ophthalmic device 1 according to the present disclosure. FIG. 1 is a diagram showing the optical systems at time of tonometry, and FIG. 2 is a diagram showing the optical systems at time of eye refraction test. Then, FIG. 3A-3D are diagrams which describe details of an examination window 30, and FIG. 4 is a block diagram which illustrates an entire configuration of the ophthalmic device including a control system according to the embodiment of the present disclosure. With reference to these FIGS. 1-4, the ophthalmic device according to the embodiment of the present disclosure will be described below.

As shown in FIG. 4, the ophthalmic device 1 comprises a head section 50 in which optical systems configured to examine a subject's eye E are disposed, and a main body 60 which is configured to control the optical systems and the like in the head section 50, and comprises a monitor 650 etc. that displays a shot image of an anterior segment and an examination result. At a time of an examination, the head section 50 is moved, in X, Y, and Z directions (side to side, up and down, and back and forth directions) relative to the main body 60 to examine the subject's eye E.

(Tonometry Optical System)

FIG. 1 shows a whole optical system at a time of tonometry for the subject's eye E (tonometry optical system 10). The tonometry optical system 10 comprises: an alignment optical system 100 constituted from a light source 101 in profile sensors 107 and 108; an observation optical system 300 constituted from light sources 301 and 302 to a two-dimensional image sensor (CCD) 306; a fixation optical system 400 constituted from a light source 401 to a mirror 404; and an intraocular pressure optical system 200 constituted from a light source 201, a nozzle 205 to a flat glass 206, and configured to detect a degree of cornea deformation of the subject's eye. As shown in FIG. 1, each of the optical systems of the tonometry optical system 10 has a configuration in which a part of each of the optical systems is shared with the eye refraction test optical system 20. Further, the examination window 30 is rotated so that the nozzle 205 for tonometry is set in position.

(Alignment Optical System 100)

In the alignment optical system 100, light from the light source 101 is reflected by a hot mirror 102, passes through an objective lens 103, and is reflected by a hot mirror 104. Then, the light passes through the flat glass 206 and an opening of the nozzle 205, and is irradiated to a cornea of the subject's eye E. In the present embodiment, an LED which emits infrared light is implemented as the light source 101.

Light reflected by the cornea is received by a lens 105 and the profile sensor 107 that are a first detection section, and a lens 106 and the profile sensor 108 that are a second detection section, wherein the first detection section and the second detection section are arranged symmetrically relative to a main optical axis O1. As shown in FIG. 4, signals obtained by the profile sensors 107 and 108 are processed in a controller 600 of the main body 60, causing an XYZ drive control unit 630 to conduct an XYZ alignment (fine adjustment) of the head section 50 relative to the subject's eye E. Although described later, the alignment of the head section 50 relative to the subject's eye E is controlled, such that on examiner sees a bright spot of alignment light on an anterior segment image which is displayed on a monitor 650 and conducts a rough alignment by operating a joystick 640 provided in the main body 60, and when the bright spot enters a predetermined range, upon which the XYZ drive control unit 630 is caused to conduct an XYZ automatic alignment.

(Observation Optical System 300)

In the observation optical system 300 of FIG. 1, an anterior segment region of the subject's eye E including the cornea is irradiated by the light sources 301 and 302 which are disposed on a subject's eye E side of the head section 50; an image of the anterior segment of the subject's eye E is obtained by an objective lens 303, an imaging lens 305, and the two-dimensional image sensor (CCD) 306; and the obtained, anterior segment image of the subject's eye E is displayed on the monitor 650 (see FIG. 4). Although an LED which emits infrared light is implemented as the light sources 301 and 302, light whose wavelength is shorter than that of the alignment light source 101 is implemented. Accordingly, the hot mirror 104 allows the light for observation (observation light) to penetrate therethrough, and reflects the light for alignment (alignment light, light from the light source 101). Further, a wavelength range of a dichroic mirror 304 for reflection/penetration is set so as to allow the observation light to penetrate therethrough. Consequently, the alignment light and the observation light are appropriately separated, enabling each measurement to be conducted.

(Fixation Optical System 400)

In the fixation optical system 400, light from the light source 401 (fixation light) is reflected by a hot mirror 402, passes through a relay lens 403, and is reflected by the reflecting mirror 404. Then, the light penetrates a hot mirror 506, is reflected by the dichroic mirror 304, travels along the main optical axis O1, passes through the objective lens 303 and the hot mirror 104, and is formed into an image on the comes of the subject's eye E. Therefore, it is preferable that positions of the light source 401 and the cornea of the subject's eye E are approximately conjugate to each other. The subject's eye, E is caused to fixate according to the fixation light, enabling an examination of an eye characteristic such as tonometry. An LED which emits visible light which the subject can see is implemented as the light source 401.

(Intraocular Pressure Optical System 200)

In the intraocular pressure optical system 200, a part of light from the light source 201 (deformation detecting light) penetrates a half mirror 202. Then, the light penetrates the hot mirror 102 and the objective lens 103, is reflected by the hot mirror 104, travels along the main optical axis O1, passes through the flat glass 206 and the opening of the nozzle 205, and is irradiated to the cornea of the subject's eye E. The light irradiated to the cornea is reflected by the cornea, and on a reverse route, i.e., passes through the opening of the nozzle 205 and the flat glass 206, is reflected by the hot mirror 104, and passes through the objective lens 103 and the hot mirror 102. A part of the light is reflected by the half mirror 202, and received at a light receiving element 204 by a condenser lens 203. Although described later, at the time of tonometry, compressed air is puffed toward the cornea of the subject's eye E from the nozzle 205. Since the cornea is displaced and deformed when the air is puffed thereto, an amount of light received by the light receiving element 204 changes. An intraocular pressure value of the subject's eye E is calculated according to a degree of a change in the amount of light. Although an LED which emits infrared light is also implemented as the light source 201, light whose wavelength is longer than that of the observation light and shorter than that of the alignment light is selected and implemented. As such, by setting the wavelength of each of the alignment light, the observation light, the fixation light, and the deformation detecting light (the light from the light source 201), and setting reflection/penetration characteristics of the hot mirrors 102, 104, 506, and 402 and the dichroic mirror 304 appropriately, of those four lights is configured to travel along a corresponding one of appropriate optical paths.

(Eye Refraction Test Optical System)

FIG. 2 shows a whole optical system at a time of eye refraction test of the subject's E (eye refraction test optical system 20). The eye refraction test optical system 20 comprises: the alignment optical system 100 constituted from the light source 101 to the profile sensors 107 and 108; the observation optical system 300 constituted from the light sources 301 and 302 to the two-dimensional image sensor (CCD) 306; the fixation optical system $00 constituted from fixation target 512 to a light source 514, a relay lens 403, and a mirror 404; and an eye refractive power optical system 500 constituted from a light source 501 to a flat glass 511, and configured to detect an eye refractivity of the subject's eye E. As shown in FIG. 2, each of the optical systems of the eye retraction test optical system 20 has a configuration in which a part of each of the optical systems is shared with the tonometry optical system 10. Further, the examination window 30 is rotated so that the flat glasses 510 and 511 for eye refraction test are set in position.

Since the alignment optical system 100 and the observation optical system 300 are the same as those at the time of tonometry described above, the descriptions will be omitted herein. The fixation optical system 400 is partially different from that at the time of tonometry, and hence it will be described below.

(Fixation Optical System 400; Eye Refraction Test)

When eye refraction test is conducted, the light source 401 which was used tonometry is turned off, and the light source 514, which is another light source, is turned on. Light from the light source 514 is turned into parallel light in a collimator lens 513 and is irradiated to the fixation target 512. The light from the fixation target 512 penetrates the hot mirror 402 and the relay lens 403. Then, the light is reflected by the mirror 404, penetrates the hot mirror 506, is reflected by the dichroic mirror 304, travels along the main optical axis O1, penetrates the objective lens 303, the hot mirror 104, and the flat glasses 511 and 510, and is formed into an image on the retina of the subject's eye E. Therefore, is preferable that positions of the fixation target 512 and the retina of the subject's eye E are approximately conjugate to each other. The subject's eye E is fixated according to the fixation target 512. When the eye refraction test is conducted, a fixation target section (the fixation target 512, the collimator lens 513, and the light source 514) is moved by a fixation target control unit 680 (see FIG. 4) so as to once make positions of the fixation target and the retina of the subject's eye E approximately conjugate to each other to fixate the subject's eye E. Thereafter, the fixation target section is moved for a predetermined distance to create as fogging state, and the eye refractive power is examined. Therefore, the fixation target section is movable back and forth along its optical axis according to a signal from the controller 600 (see FIG. 4). An LED which emits visible light which the subject can see and whose wavelength is shorter than that of the light source 401 is implemented as the light source 514.

(Eye Refractive Power Optical System 500)

In the eye refractive power optical system 500, light from the light source 501 (reflector light) is condensed in a condenser lens 502, is reflected by the mirror 503, passes through a hole located at a center of a holed mirror 504, and penetrates a parallel flat glass 505 which is disposed aslant relative to an optical axis O2 and rotates about the optical axis O2 by a driver which is not shown. Then, the light is reflected by the hot mirror 506 and the dichroic mirror 304, travels along the optical axis O1, penetrates the objective lens 303, the hot mirror 104, and the flat glasses 511 and 510, and is irradiated to the retina of the subject's eye E. Then, reflected light from the retina of the subject's eye E, on a route reverse to the irradiation route, penetrates the flat glasses 510 and 511, the hot mirror 104 and the objective lens 303, is reflected by the dichroic mirror 304 and the hot mirror 506, travels along the optical axis O2, and penetrates the parallel flat glass 505. Then, the light, is reflected by the holed mirror 504, and after penetrating a lens 507, is formed into an image in a form of a ring (ring image) by a ring lens 508 in a two-dimensional image sensor (CCD) 509. As the light source 501, infrared light whose wavelength is longer than that of the alignment light (the light source 101) and the observation light (the light sources 301 and 302) is implemented. Although an SLD (superluminescent diode) having a wavelength of 870 nm is implemented in the present embodiment, the light source 501 is not limited to the SLD, and the LED which is implemented as the light source 101, etc. and a laser diode (LD) may be implemented.

Here, the parallel flat glass 505 is disposed at a position where the parallel flat glass 505 and a pupil of the subject's eye E are conjugate to each other. When the reflector light (the light from the light source 501) enters the parallel flat glass 505 disposed aslant relative to the optical axis O2, the light is refracted and deviated for a predetermined distance (e.g., Δ H) relative to the optical axis O2. As described above, since the parallel flat glass 505 rotates about the optical axis O2, the reflector light which penetrates the parallel flat glass 505 rotates with a radius of Δ H at a position of the parallel flat glass 505. Since the parallel flat glass 505 is disposed at the position which makes the parallel flat glass 505 and the position of the pupil of the subject's eye E conjugate to each other, the reflector light is irradiated on the retina of the subject's eye, while rotating with a predetermined (constant) radius (e.g., Δ h) at the position of the pupil of the subject's eye E. Therefore, the reflector light is formed on the retina of the subject's eye E into a circular image whose size and shape are determined according to the refractive power of the subjects eye E. Since the CCD 509 is disposed at a position which makes the CCD 509 and the retina of the subjects eye E conjugate to each other, by analyzing the ring image obtained in the CCD 509, the refractive power of the subject's eye E can be measured.

(Examination Window 30)

Figure 3A:
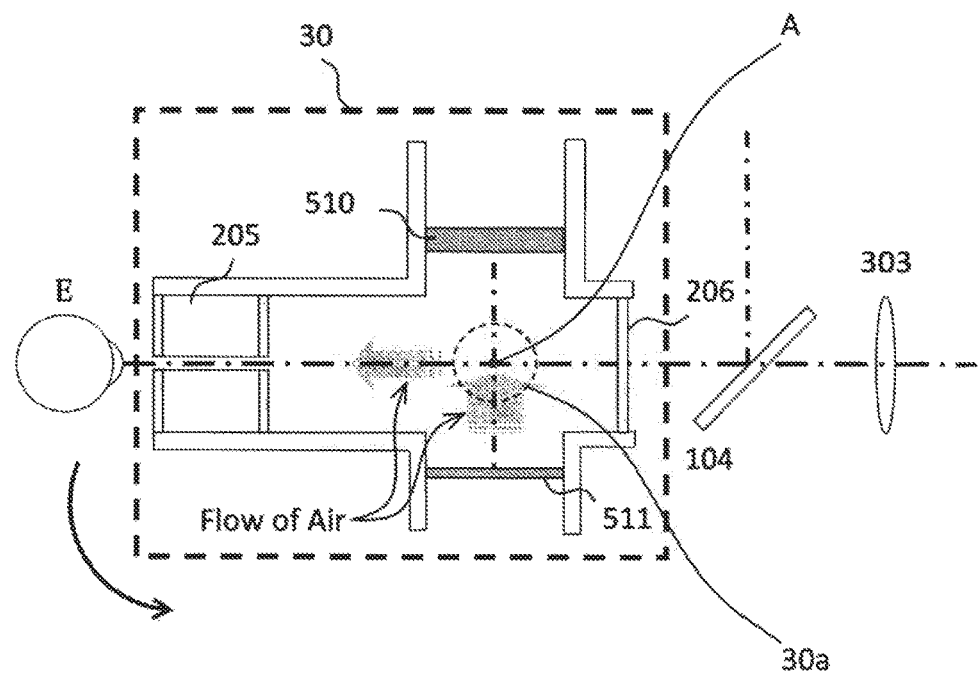
FIG. 3A is as cross sectional view of an examination window according to the embodiment (at time of tonometry)
Figure 3B:
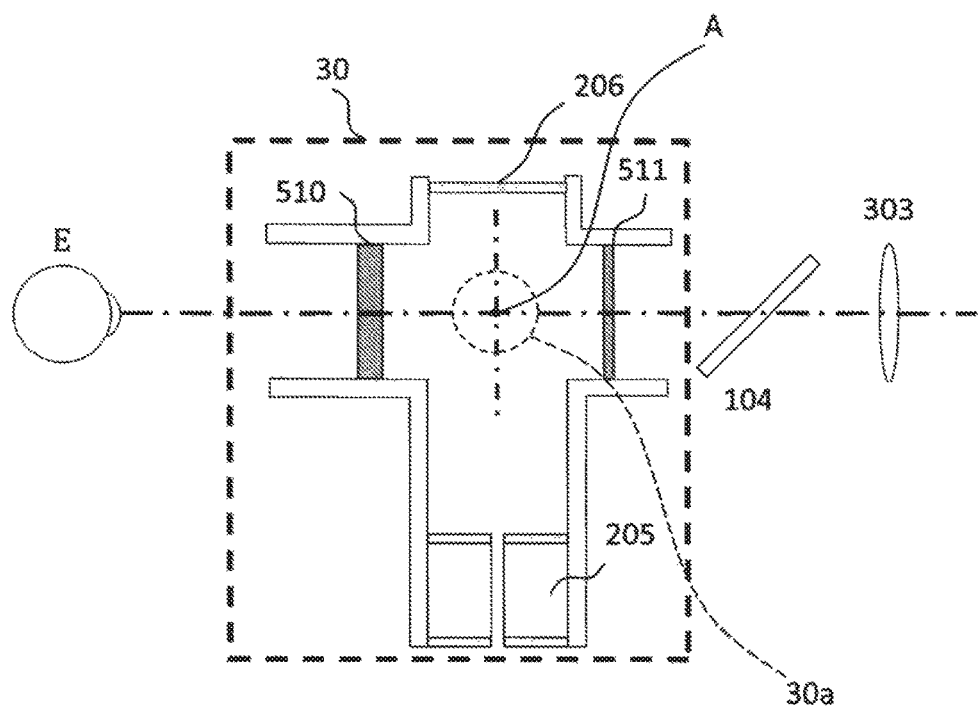
FIG. 3B is a diagram viewing the examination window according to the embodiment from as subject's eye E side (at time of tonometry)
Figure 3C:
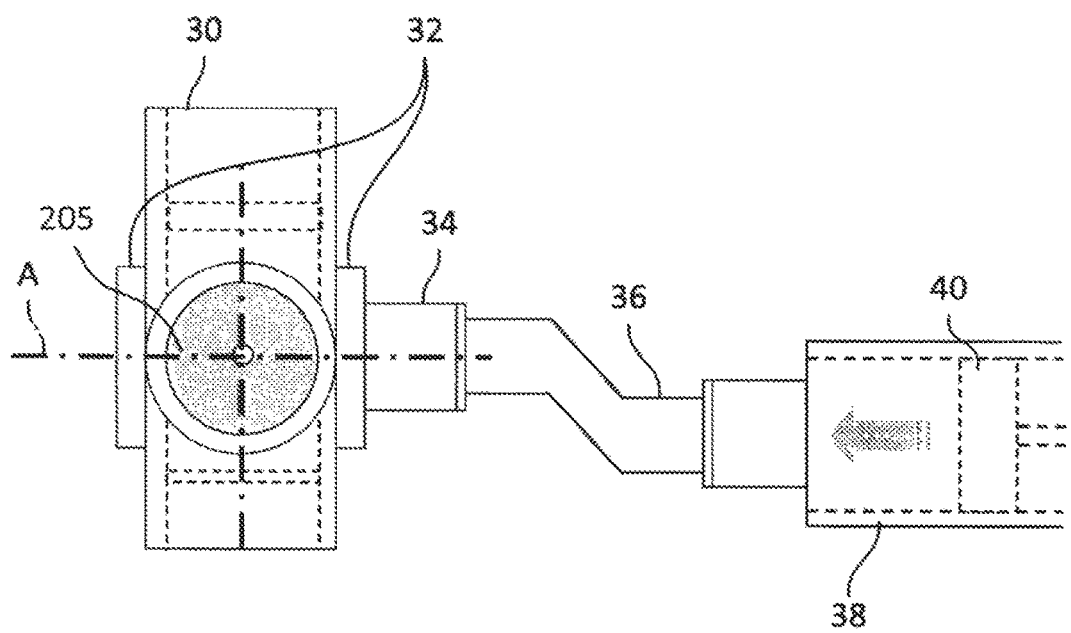
FIG. 3C is a cross sectional view of the examination window according to the embodiment (at time of eye refraction test)
Figure 3D:
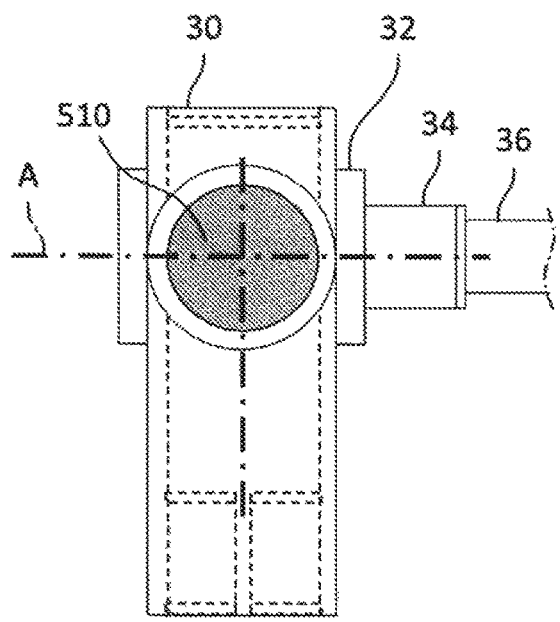
FIG. 3D is a diagram viewing the examination window according to the embodiment from the subject's eye E side (at time of eye refraction test)
Figure 4:
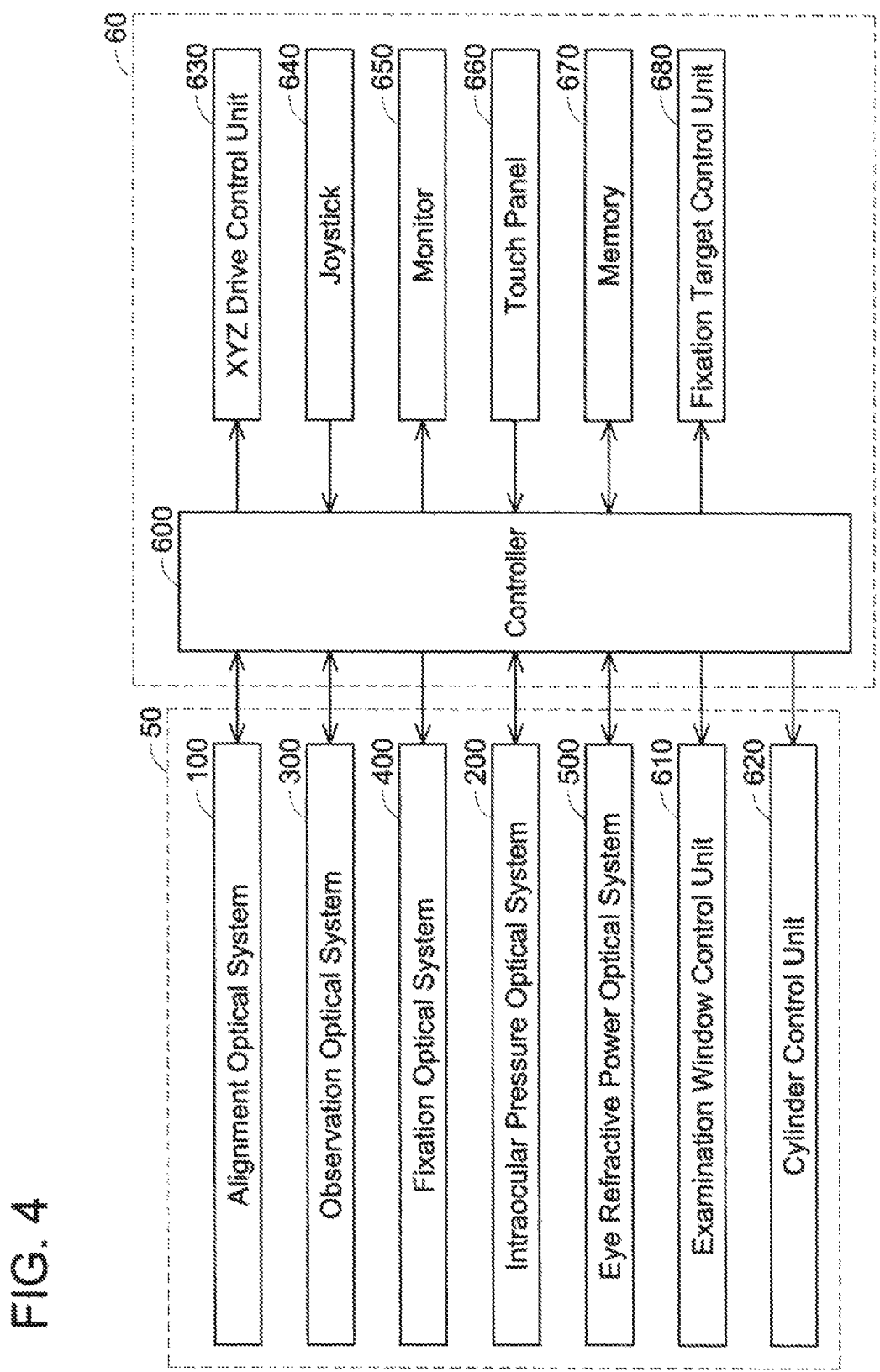
FIG. 4 is a block diagram of as control system of the ophthalmic device according to the embodiment of the present application.

With reference to FIGS. 3A to 3D, the examination window 30 will be described. FIGS. 3A to 3D are diagrams which illustrate details of the examination window 30 according to the present embodiment. FIGS. 3A and 3C show the examination window 30 at the time of tonometry, and FIGS. 3B and 3D show the examination window 30 at the time of eye refraction test. FIGS. 3A and 3B are each a cross sectional view of the examination window 30 seen from a lateral side, and FIGS. 3C and 3D each are a view of the examination window 30 from the subject's eye E. As Shown in FIGS. 3A and 3B, the examination window 30 is constituted of the nozzle 205 and the flat glass 206 which are set in position at the time of tonometry, and the flat glasses 510 and 511 which are set in position at the time of eye refraction test. Further, the examination window 30 is provided with an inflow hole 30a into which air flows. As shown in FIG. 3C, the examination window 30 is connected to a cylinder 38 via a bearing 34 and a tube 36. The inflow hole 30a, the bearing 34, and the tube 36 are in communication with each other. Due to thus, a cylinder control unit 620 controls to move a piston 40 within the cylinder 38 by using a solenoid net shown for example, such that compressed air flows from the cylinder 38 through the tube 36, bearing 34, and inflow hole 30a to enter the nozzle 205 and the air is puffed toward the cornea of the subject's eye E. As shown in FIGS. 3C and 3D, a rotation mechanism 32 is coupled to the examination window 30. Operation of the rotation mechanism 32 is controlled by an examination window control unit 610 (see FIG. 4). The examination window 30 is configured to rotate around a center axis A of the inflow hole 30a by the rotation mechanism 32 disposed on right and left sides of the examination window 30. Notably, a center axis of air passage of an flowing from the inflow hole 30a and a center axis of the bearing 34 coincide with the center axis A of the inflow hole 30a.

As shown in FIGS. 3A to 3D, since the nozzle 205 and the flat glass 206 are set in position at the time of tonometry (FIGS. 3A and 3C), and the flat glasses 510 and 511 are set in position at the time of eye refraction test (FIGS. 3B and 3D), none of the optical elements are shared in each of the examinations in the examination window 30. Further, there is no change of optical path by the rotation of the examination window 30 for switching the examinations. Therefore, even if a position of an optical element in the examination window 30 is displaced by the rotation of the examination window 30, an effect of the position displacement can be suppressed.

(Operation Flow)

Figure 5:
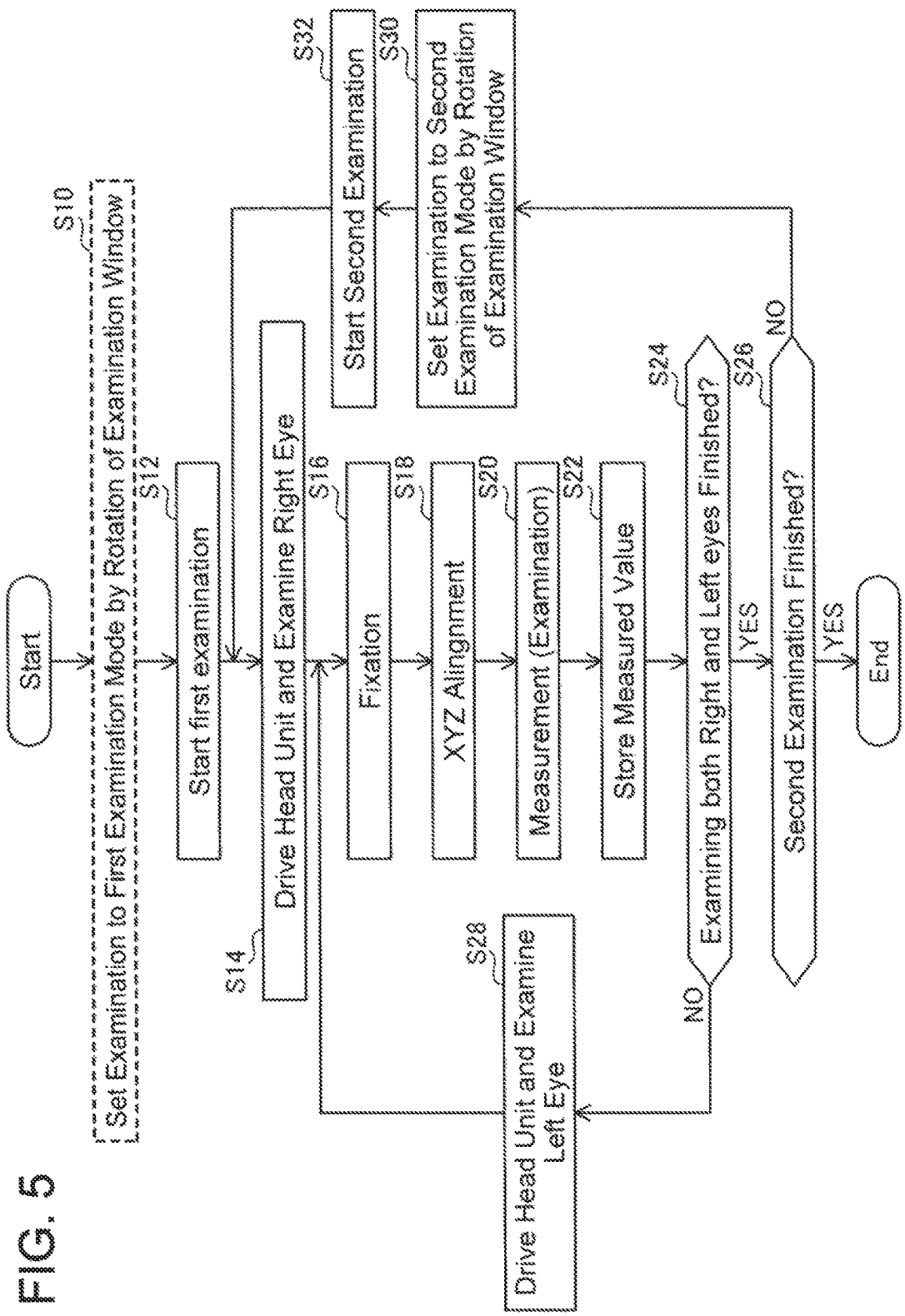
FIG. 5 is a diagram which illustrates an operation flow of the ophthalmic device according to the embodiment of the present application.

FIG. 5 illustrates an operation flow of the ophthalmic device according to the present embodiment. Notably, in the present embodiment, the eye refraction test as the first examination and the tonometry as the second examination are conducted. Notably, the examinations are initiated by operation of a touch panel 660 (see FIG. 4).

In S10, in order to conduct the eye refraction test as the first examination, the examination window 30 is rotated so as to set the flat glasses 510 and 511 in position as shown in FIG. 2 and FIGS. 3B and 3D (first examination mode). If the examination window 30 has already been disposed in the state for the eye refraction test, S10 is omitted.

In S12, the eye refraction test being the first examination is started. Although not shown in the operation flow, at tins occasion, the observation light sources 301, 302, and the alignment light source 101, the fixation target light source 514 and the eye refraction test light source 501 are lighted.

In S14, the head section 50 is moved by using a joystick 640 such that a right eye of a patient is displayed on the monitor 650. Then the head section 50 is roughly aligned in X, Y, and Z directions so as to include the bright spot on the cornea in a predetermined area.

In S16, the fixation target 512 causes the right eye to fixate. In case of the eye refraction test, the refractive power is measured also at this occasion, and the fixation target section (512 to 514) is moved such that the fixation target 512 is positioned to conjugate with the retina of the subject's eye E based on the obtained value of eye refractive power. Thus, the subject's eye E is fixated.

In S18, an alignment state is detected by signals obtained by the profile sensor 107 and the profile sensor 108, and the detection result is used for the XYZ control unit 630 within the main body to perform the XYZ alignment of the head section 50.

Once the XYZ alignment has been complete, the measurement is started in S20. In case of the eye refraction test, the measurement of eye refractive power is conducted after, in order to set the subject's eye E in an open state, the fixation target part (512 to 514) is moved along the optical axis for a predetermined distance to create a fogging state.

In S22, the measured value, is stored in a memory 670.

In S24, determination is made in regards to whether both the fell and right eyes have been examined. When the right eye has only been examined, in S28, the head section 50 is moved to a left eye side, similarly to the right eye, the refractive power of the left eye is measured in S18 to S22 and the measured value is stored in the memory 670.

Upon completion of the measurement for both the left and right eyes, in S26, determination is made in regards to whether the tonometry being the second examination has been finished.

When the tonometry being the second examination has not been finished, in S30, the examination window 30 is rotated such that the nozzle 205 and the plane glass 206 are positioned as shown in FIG. 1 and FIGS. 3A and 3C (second examination mode). In S32, the tonometry being the second examination is started. Here, although not shown in the operation flow, the fixation light source 514 used for the eye refraction test is extinguished, and instead the fixation light source 401 is lighted.

In S14, similarly to the eye refraction test, the head section 50 is moved by using the joystick 640 such that the right eye of the subject is displayed on the monitor 650. Then the head section 50 is roughly aligned in the X, Y, and Z directions so as to include the bright spot on the cornea generated by the alignment light in a predetermined area.

In S16, the fixation light from the light source 401 causes the subject's eye E to fixate.

In S18, similarly to the eye refraction test, the alignment state is detected from signals obtained by the profile sensors 107 and 108, the detected result is used for the XYZ drive control unit 630 within the main body 60 to perform XYZ alignment of the head section 50.

Upon completion of the XYZ alignment, in S20, the measurement is started. As described above, the light from the light source 201 is irradiated onto the cornea of the subject's eye E, and its reflected light is received by the light receiving element 204. Then, the cylinder control unit 620 controls the piston 40 within the cylinder 38 shown in FIG. 3C to be activated, air compressed within the cylinder 38 enters an air passage of the examination window 30 via the tube 36 and the inflow hole 30a, and the air is puffed through the nozzle 205 toward the cornea of the subject's eye E. The puffed air causes the cornea to displace and deform, changing the amount of light received by the light receiving element 204 (the puffed air flattens the cornea, increasing the amount of light received by the light receiving element 204). Time required for a light receiving signal obtained in the light receiving element 204 to become a predetermined value is measured, and in S22, the measured value is stored in the memory 670. Because an intraocular pressure value is in correlation with the time taken from when the air is puffed until the light receiving signal becomes the predetermined value, the intraocular pressure value of the subject's eye E can be estimated from the stored measured value (i.e., time).

In S24, similarly to the eye refraction test whether both the left and right eyes have been measured is determined. When the right eye only has been measured, in S28, the head section 50 is moved to the left eye side, the tonometry is conducted for the left eye in S18 to S22 similar to the right eye, and its result is stored in the memory 670.

When the measurements for the left and right eyes have been finished, in S26, whether the tonometry being the second examination has been finished is determined. When the tonometry being the second examination has been finished, the whole measurement is finished.

Notably, in the above embodiment, the first examination is the eye refraction test, and the second examination is the tonometry, however, this does not imply any limitation, and the two examinations can be vice versa. Further, both the first and second examinations may not necessarily be conducted, only one examination may be conducted. An examination that is necessary may be suitably determined, and conducted. In the embodiment, the examination is started with the right eye, however, the examination may be started with the left eye, or only one eye may be examined.

While specific examples of the present disclosure have been described above in detail, these examples are merely illustrative and specific descriptions place no limitation on the scope of the patent claims. It should be understood that the present disclosure may be performed in aspect(s) which includes various changes, modifications, improvements based on knowledge of those skilled in the art. It should also be understood that any and all such changes, modifications, and improvements which do not depart from the spirit and scope of the present disclosure are therefore covered by and embraced within the present disclosure.

Although in the embodiment, the refractive power test is conducted as the first examination, the first examination is not limited to this. For example, a kerato optic system may be disposed, the kerato optic system being configured by arranging a plurality of light sources along a circumference with a predetermined radius in the examination window 30 on a subject's eye E side, to irradiate a plurality of light beams circumferentially onto the cornea of the subject's eye E and measure a curvature radius of the cornea based on a plurality of bright spots that are irradiated on the cornea by using the two-dimensioned imaging element (CCD) 306 in the observation optical system. Further, the kerato optic system may be added to the refractive power optic system, and, the refraction test and the kerato examination may be performed for the first examination. In addition, by disposing a topocone that examines a cornea shape, instead of the kerato optic system, and a cornea shape map (topomap) may h generated instead of a kerato value, and displayed on the monitor 650.

What is claimed is:

1. An ophthalmic device configured to examine at least two eye characteristics including intraocular pressure, the ophthalmic device comprising:
   an examination optical system configured to obtain examination information of a subject's eye when the at least two eye characteristics of the subject's eye are examined; and
   an examination window configured to switch examinations of the at least two eye characteristics and does not include a dichroic mirror that is shared when examining the at least two eye characteristics,
   wherein
   the examination optical system is arranged outside of the examination window,
   the examination window is capable of rotating independently of the examination optical system, and
   the examinations of the at least two eye characteristics are switched by rotation of the examination window.

2. The ophthalmic device as in claim 1, wherein
   the examination window comprises an inflow hole into which air flows from outside of the examination window when the intraocular pressure is examined, and
   the examination window is configured to rotate around a center axis of the inflow hole.

3. The ophthalmic device as in claim 1, wherein
   the at least two eye characteristics include a first eye characteristic and a second eye characteristic different from the first eye characteristic, the second eye characteristic being the intraocular pressure,
   the examination optical system comprises:
      a first examination optical system used to examine the first eye characteristic; and
      a second examination optical system used to examine the second eye characteristic,
   the examination window is capable of switching between a first state and a second state different from the first state, and the first eye characteristic is examined by using the examination window and the first examination optical system when the examination window is in the first state; and the second eye characteristic is examined by using the examination window and the second examination optical system when the examination window is in the second state.

4. The ophthalmic device as in claim 3, wherein the examination optical system comprises a common observation optical system configured to serve as:
   a first observation optical system configured to observe the subject's eye when the first eye characteristic is examined; and
   a second observation optical system configured to observe the subject's eye when the second eye characteristic is examined.

5. The ophthalmic device as in claim 3, wherein the examination optical system comprises a common index optical system (fixation optical system) configured to serve as:
   a first index optical system (fixation optical system) configured to cause the subject's eye to fixate when the first eye characteristic is examined, and
   a second index optical system (fixation optical system) configured to causes the subject's eye to fixate when the second eye characteristic is examined.

6. The ophthalmic device as in claim 3, wherein the examination optical system comprises a common alignment optical system configured to serve as:
   a first alignment optical system configured to conduct alignment when the first eye characteristic is examined, and
   a second alignment optical system configured to conduct alignment when the second eye characteristic is examined.

7. The ophthalmic device as in claim 3, wherein the first eye characteristic is refractive power of the subject eye.

8. An ophthalmic device comprising:
   a first examination optical system configured to obtain examination information of a first eye characteristic of a subject's eye when the first eye characteristic is examined,
   a second examination optical system configured to obtain examination information of a second eye characteristic of the subject's eye when the second eye characteristic is examined, the second eye characteristic being different from the first eye characteristic, and
   an examination window capable of switching between a first state and a second state different from the first state and does not include a dichroic mirror that is shared when examining the at least two eye characteristics, wherein
   the first eye characteristic is examined by using the examination window and the first examination optical system when the examination window is in the first state; and
   the second eye characteristic is examined by using the examination window and the second examination optical system when the examination window is in the second state,
   wherein an optical axis of the first examination optical system and an optical axis of the second examination optical system are not changed even when the examination window is switched from the first state to the second state, and
   the optical axis of the first examination optical system and the optical axis of the second examination optical system are not changed even when the examination window is switched from the second state to the first state.

* * * * *